(12) United States Patent
Bibillo et al.

(10) Patent No.: US 11,519,026 B2
(45) Date of Patent: Dec. 6, 2022

(54) METHODS FOR REMOVAL OF ADAPTOR DIMERS FROM NUCLEIC ACID SEQUENCING PREPARATIONS

(71) Applicant: Roche Sequencing Solutions, Inc., Pleasanton, CA (US)

(72) Inventors: Arkadiusz Bibillo, Cupertino, CA (US); Randall W. Davis, Pleasanton, CA (US)

(73) Assignee: Roche Sequencing Solutions, inc., Pleasanton, CA (US)

( * ) Notice: Subject to any disclaimer, the term of this patent is extended or adjusted under 35 U.S.C. 154(b) by 625 days.

(21) Appl. No.: 16/263,726

(22) Filed: Jan. 31, 2019

(65) Prior Publication Data

US 2019/0161794 A1    May 30, 2019

Related U.S. Application Data

(63) Continuation of application No. PCT/EP2017/069308, filed on Jul. 31, 2017.

(60) Provisional application No. 62/369,352, filed on Aug. 1, 2016.

(51) Int. Cl.
| | | |
|---|---|---|
| *C12Q 1/68* | (2018.01) | |
| *C12Q 1/6869* | (2018.01) | |
| *C12Q 1/6855* | (2018.01) | |
| *C12Q 1/6806* | (2018.01) | |
| *C12Q 1/6848* | (2018.01) | |

(52) U.S. Cl.
CPC ......... *C12Q 1/6869* (2013.01); *C12Q 1/6806* (2013.01); *C12Q 1/6848* (2013.01); *C12Q 1/6855* (2013.01); *C12Y 207/07007* (2013.01); *C12Y 301/11002* (2013.01); *C12Y 301/11003* (2013.01); *C12Y 301/11005* (2013.01); *C12Y 301/11006* (2013.01); *C12Y 301/15* (2013.01); *C12Y 301/21* (2013.01); *C12Y 301/22001* (2013.01); *C12Y 301/25001* (2013.01)

(58) Field of Classification Search
None
See application file for complete search history.

(56) References Cited

U.S. PATENT DOCUMENTS

| | | | | |
|---|---|---|---|---|
| 5,834,233 | A  * | 11/1998 | Molin et al. ............. | C12N 9/22 435/69.1 |
| 2004/0101838 | A1* | 5/2004 | Thompson ............ | C12Q 1/6837 435/6.1 |
| 2006/0057569 | A1* | 3/2006 | Charle ................. | C12Q 1/6837 435/6.12 |
| 2006/0292611 | A1* | 12/2006 | Berka ................ | C12N 15/1093 435/6.1 |
| 2014/0199690 | A1* | 7/2014 | Zhao ..................... | C12Q 1/683 435/6.11 |

FOREIGN PATENT DOCUMENTS

| | | |
|---|---|---|
| GB | 2532749 A | 6/2016 |
| WO | 2007/145612 A1 | 12/2007 |
| WO | 2008/015396 A2 | 2/2008 |
| WO | 2009/098037 A1 | 8/2009 |

OTHER PUBLICATIONS

International Search Report and Written Opinion dated Nov. 7, 2017 in corresponding PCT/EP2017/069308 filed Jul. 31, 2017, pp. 1-11.

* cited by examiner

*Primary Examiner* — Bradley L. Sisson
(74) *Attorney, Agent, or Firm* — Eric Grant Lee; Olga Kay (57) ABSTRACT

Sequencing adaptors and methods are provided for preparation of polynucleotides for sequencing. The sequencing adaptors contain a portion of a recognition sequence for a methyl-dependent endonuclease. Unwanted adaptor dimers that form during ligation of adaptors to target polynucleotides produce a complete restriction sequence and are cleaved by the endonuclease, followed by exonuclease digestion, thereby removing the dimers.

18 Claims, 1 Drawing Sheet

METHODS FOR REMOVAL OF ADAPTOR DIMERS FROM NUCLEIC ACID SEQUENCING PREPARATIONS

RELATED APPLICATIONS

This application is a continuation of International Patent Application No. PCT/EP2017/069308, filed Jul. 31, 2017, which claims priority to U.S. Provisional Application Ser. No. 62/369,352, filed on Aug. 1, 2016, the entire contents of each is incorporated herein by reference as if set forth in its entirety.

FIELD OF THE INVENTION

The invention relates to methods and compositions for removal of unwanted adaptor dimers from a nucleic acid sequencing sample preparation mixture.

BACKGROUND

Major DNA sequencing technologies rely on the attachment of specific DNA adaptors to the ends of sample DNA fragments to create polymerase primer sites, to add sample capture sites, to "barcode" samples, and to add calibration sites to samples, among many possible uses. Adaptor nucleic acids are ligated to each end of a DNA sample to be sequenced. The creation of adaptor ligated DNA fragments often include adaptors ligating to each other, forming unwanted "adaptor dimers."

Currently, adaptor dimers are removed by small fragment cleanup steps, such as use of magnetic beads to capture and separate large polynucleotide fragments from small fragments. Such a method is not sequence based and is therefore nonspecific and inefficient. If the sample is circularized, non-circularized adaptors may be depolymerized from their exposed ends by treatment with exonucleases. In particular, the removal of circularized adaptor dimers from a set of near- or similar-sized DNA sample fragments is especially difficult. Cleanup steps do not efficiently remove the dimers based on size or take considerable time. Further, circular adaptors cannot be depolymerized by exonucleases since they do not have an exposed end.

More efficient and specific methods for removal of unwanted adaptor dimers are needed.

BRIEF SUMMARY OF THE INVENTION

Adaptors for polynucleotide sequencing are provided as well as methods and kits for their use in sequencing methods. The adaptors and methods described herein may be used to produce polynucleotide samples for sequencing without adaptor dimers or with very low levels of adaptor dimers, which would otherwise interfere with or reduce efficiency of polynucleotide sequencing methods.

In one aspect, a method is provided for preparing target DNA duplexes for sequencing. In the methods disclosed herein, adaptors include a portion of a methyl-dependent endonuclease recognition sequence, which when covalently joined in an adaptor dimer, will form the complete recognition sequence and will be subject to digestion by the endonuclease. Adaptor dimers are removed by digestion by the methyl-dependent endonuclease, followed by exonuclease digestion. Adaptors linked to target polynucleotides for sequencing are not sensitive to digestion by the endonuclease and exonuclease enzymes, and thus only the unwanted adaptor dimers are removed from the sample.

In one embodiment, the method includes: (a) covalently linking double-stranded polynucleotide duplex regions of a plurality sequencing adaptors to first and second ends of a plurality of blunt-ended target DNA duplexes, thereby producing a plurality of adaptor-linked target DNA duplexes with a sequencing adaptor covalently linked at each end of the target DNA duplex, wherein the double-stranded polynucleotide duplex region of each adaptor includes a portion of a recognition sequence for a methyl-dependent endonuclease at its end, wherein a complete recognition sequence for the methyl-dependent endonuclease will be formed if the duplex regions of two adaptors are covalently linked together to produce an adaptor dimer; and (b) removing adaptor dimers, if any, by digestion with a methyl-dependent endonuclease followed by digestion with one or more exonuclease(s).

In another embodiment, the method includes: (a) providing a plurality of sequencing adaptors, wherein each of said adaptors includes a double-stranded polynucleotide duplex region, wherein the double-stranded polynucleotide duplex region includes a portion of a recognition sequence for a methyl-dependent endonuclease at its end, wherein a complete recognition sequence for the methyl-dependent endonuclease will be formed if the duplex regions of two adaptors are covalently linked together to produce an adaptor dimer; (b) covalently linking the duplex regions of said sequencing adaptors to first and second ends of a plurality of blunt-ended target DNA duplexes, thereby producing a plurality of adaptor-linked target DNA duplexes with a sequencing adaptor covalently linked at each end of the target DNA duplex; and (c) removing adaptor dimers, if any, by digestion with a methyl-dependent endonuclease followed by digestion with one or more exonuclease(s).

The adaptors may include a single-stranded hairpin region or may be linear. In one embodiment, each of the adaptors includes a single-stranded polynucleotide hairpin region and the double-stranded polynucleotide duplex region. In another embodiment, each of the adaptors is a linear polynucleotide that includes first and second polynucleotide strands, wherein each adaptor includes the double-stranded polynucleotide duplex region and a 3' overhang region, wherein the first strand includes the 3' overhang region and includes a modified nucleotide that is resistant to exonuclease digestion (e.g., a thionated nucleotide) at or near the 3' end and the second strand, which is part of the polynucleotide duplex, includes a modified nucleotide that is resistant to exonuclease digestion (e.g., a thionated nucleotide) at or near the 5' end.

In some embodiments, the double-stranded polynucleotide duplex region in each of the adaptors includes a first strand with a 5' end hybridized to a second strand with a 3' end, wherein the first strand includes the sequence GG at the 5' end hybridized to the sequence $C_{Me}C$ at the 3' end of the second strand. The methyl-dependent endonuclease may be, for example, MspI or MspII, wherein adaptor dimers include the recognition sequence $CC_{Me}GG$.

In some embodiments, the double-stranded polynucleotide duplex region in each of the adaptors includes a first strand with a 5' end hybridized to a second strand with a 3' end, wherein the first strand includes the sequence TC at the 5' end hybridized to the sequence $GA_{Me}$ at the 3' end. The methyl-dependent endonuclease may be, for example, DpnI or DpnII, wherein adaptor dimers include the recognition sequence $GA_{Me}TC$.

In some embodiments, the exonuclease(s) used for digestion of cleaved adaptor dimers includes Exonuclease VII, Exonuclease III, and/or T5 Exonuclease. In some embodiments, Exonuclease III and Exonuclease VII are used. In some embodiments, Exonuclease III and T5 Exonuclease are used.

In some embodiments, a ligase enzyme is used to covalently link the double-stranded polynucleotide duplex regions of the sequencing adaptors to the first and second ends of the blunt-ended target DNA duplexes.

In various embodiments, the target DNA duplexes may include amplified target polynucleotides, non-amplified fragments of genomic DNA, copies of fragments of genomic DNA synthesized with unmethylated nucleotides, and/or cDNA transcribed from fragments of RNA. In various embodiments, the target DNA duplexes may be derived from a biological fluid or tissue sample and/or from one or more microorganism(s).

In another aspect, a method is provided for preparing a polynucleotide sample for sequencing, which method includes covalently attaching sequencing adaptors to target DNA duplexes to be sequenced, in accordance with the methods described herein, and wherein the resulting polynucleotide sample for sequencing includes less than about 1% adaptor dimers.

In another aspect, a method is provided for preparing a polynucleotide sample for sequencing, which method includes covalently attaching sequencing adaptors to target DNA duplexes to be sequenced, in accordance with the methods described herein, including hybridizing a primer to a primer binding sequence on the covalently linked adaptors and extending the primer with a DNA polymerase enzyme, thereby preparing a primer extension product for sequencing. For example, the primer may be extended to produce a complementary copy of one strand of the target DNA duplex, wherein the copy is sequenced as it is synthesized by the polymerase. In one embodiment, the primer binding sequence is in a single-stranded hairpin region of the adaptor. In another embodiment, the primer binding sequence is in a 3' single-stranded overhang region of the adaptor.

In another aspect, adaptors are provided for polynucleotide sequencing. The adaptor includes a double-stranded polynucleotide duplex region, wherein the double-stranded polynucleotide duplex region includes a portion of a recognition sequence for a methyl-dependent endonuclease at its end, and wherein a complete recognition sequence for the methyl-dependent endonuclease will be formed if the duplex regions of two adaptors are covalently linked together to produce an adaptor dimer.

In an embodiment, the adaptor includes a single-stranded polynucleotide hairpin region and the double-stranded polynucleotide duplex region, optionally including a primer binding site in the hairpin region.

In an embodiment, the adaptor is a linear polynucleotide that includes first and second polynucleotide strands, wherein the adaptor includes the double-stranded polynucleotide duplex region and a 3' overhang region, wherein the first strand includes the 3' overhang region and includes a modified (e.g., thionated) nucleotide that is resistant to exonuclease digestion at or near the 3' end and the second strand, which is part of the polynucleotide duplex, includes a modified (e.g., thionated) nucleotide that is resistant to exonuclease digestion at or near the 5' end.

In an embodiment, the double-stranded polynucleotide duplex in the adaptor includes a first strand with a 5' end hybridized to a second strand with a 3' end, wherein the first strand includes the sequence GG at the 5' end hybridized to the sequence $C_{Me}C$ at the 3' end of the second strand.

In an embodiment, the double-stranded polynucleotide duplex in the adaptor includes a first strand with a 5' end hybridized to a second strand with a 3' end, wherein the first strand includes the sequence TC at the 5' end hybridized to the sequence $GA_{Me}$ at the 3' end.

In another aspect, a method is provided for sequencing polynucleotides, the method including sequencing a polynucleotide sample that includes a plurality of adaptor-linked DNA duplexes with a sequencing adaptor as described herein covalently linked at each end of the target DNA duplex, wherein the polynucleotide sample includes less than about 1% adaptor dimers.

In another aspect, a polynucleotide sample for sequencing is provided, the sample including a plurality of adaptor-linked DNA duplexes with a sequencing adaptor as described herein covalently linked at each end of the target DNA duplex, wherein the polynucleotide sample includes less than about 1% adaptor dimers.

In another aspect, a kit is provided for polynucleotide sequencing. In some embodiments, the kit includes: (a) a plurality of sequencing adaptors as described herein; and (b) instructions for preparing target DNA duplexes for sequencing as described herein. In some embodiments, the kit further includes (c) a ligase enzyme; (d) a methyl dependent endonuclease enzyme; (e) one or more exonuclease enzyme(s); and/or (f) one or more sequencing primer(s).

DETAILED DESCRIPTION

Methods are provided for preparing adaptor-linked DNA duplexes for sequencing without significant levels of unwanted adaptor duplexes that are formed by ligation of adaptors to each other instead of to the ends of the target DNA. In the methods described herein, adaptors contain a unique sequence at the ends of a DNA duplex therein, containing a methylated nucleotide base. When adaptors are ligated together to form a dimer, these sequences form a restriction site for a methyl-dependent restriction endonuclease enzyme, providing a cleavage site for specific removal of adaptor dimers from the reaction mixture. Adaptors that are ligated to the ends of target DNA, which does not contain the remaining sequences for the restriction enzyme recognition site, are not cleaved and remain attached to the target for sequencing.

Unless defined otherwise herein, all technical and scientific terms used herein have the same meaning as commonly understood by one of ordinary skill in the art to which this invention belongs. Singleton, et al., *Dictionary of Microbiology and Molecular Biology*, second ed., John Wiley and Sons, New York (1994), and Hale & Markham, *The Harper Collins Dictionary of Biology*, Harper Perennial, NY (1991) provide one of skill with a general dictionary of many of the terms used in this invention. Any methods and materials similar or equivalent to those described herein can be used in the practice or testing of the present invention.

The practice of the present invention will employ, unless otherwise indicated, conventional techniques of molecular biology (including recombinant techniques), microbiology, cell biology, and biochemistry, which are within the skill of the art. Such techniques are explained fully in the literature, for example, *Molecular Cloning: A Laboratory Manual*, second edition (Sambrook et al., 1989); *Oligonucleotide Synthesis* (M. J. Gait, ed., 1984; *Current Protocols in Molecular Biology* (F. M. Ausubel et al., eds., 1994); *PCR: The Polymerase Chain Reaction* (Mullis et al., eds., 1994); and *Gene Transfer and Expression: A Laboratory Manual* (Kriegler, 1990).

Numeric ranges provided herein are inclusive of the numbers defining the range.

Unless otherwise indicated, nucleic acids are written left to right in 5' to 3' orientation; amino acid sequences are written left to right in amino to carboxy orientation, respectively.

Definitions

"A," "an" and "the" include plural references unless the context clearly dictates otherwise.

The term "adaptor" herein refers to a nucleic acid that is attached to both strands of a double-stranded DNA molecule. The adaptor can be composed of two distinct oligonucleotide molecules that are base-paired with one another, i.e., complementary. Alternatively, the adaptor can be composed of a single oligonucleotide that comprises one or more regions of complementarity, and one or more non-complementary regions.

The term "base pair" or "bp" as used herein refers to a partnership (i.e., hydrogen bonded pairing) of adenine (A) with thymine (T), or of cytosine (C) with guanine (G) in a double stranded DNA molecule. In some embodiments, a base pair may comprise A paired with Uracil (U), for example, in a DNA/RNA duplex.

The term "complementary" herein refers to the broad concept of sequence complementarity in duplex regions of a single polynucleotide strand or between two polynucleotide strands between pairs of nucleotides through base-pairing. It is known that an adenine nucleotide is capable of forming specific hydrogen bonds ("base pairing") with a nucleotide, which is thymine or uracil. Similarly, it is known that a cytosine nucleotide is capable of base pairing with a guanine nucleotide. "Essentially complementary" herein refers to sequence complementarity in duplex regions of a single polynucleotide strand or between two polynucleotide strands, e.g., polynucleotide strands of an adaptor wherein the complementarity is less than 100% but is greater than 90%, and retains the stability of the duplex region, e.g., under conditions for covalent linking of the adaptor to a target DNA duplex.

The term "derived from" encompasses the terms "originated from," "obtained from," "obtainable from," "isolated from," and "created from," and generally indicates that one specified material finds its origin in another specified material or has features that can be described with reference to the another specified material.

The term "duplex" herein refers to a region of complementarity that exists between two polynucleotide sequences.

The terms "first end" and "second end" when used in reference to a nucleic acid molecule, herein refers to ends of a linear nucleic acid molecule.

A "gene" refers to a DNA segment that is involved in producing a polypeptide and includes regions preceding and following the coding regions as well as intervening sequences (introns) between individual coding segments (exons).

The term "introduced," in the context of inserting a nucleic acid sequence into a cell, includes "transfection," "transformation," or "transduction" and refers to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed.

The terms "isolated," "purified," "separated," and "recovered" as used herein refer to a material (e.g., a protein, nucleic acid, or cell) that is removed from at least one component with which it is naturally associated, for example, at a concentration of at least 90% by weight, or at least 95% by weight, or at least 98% by weight of the sample in which it is contained. For example, these terms may refer to a material which is substantially or essentially free from components which normally accompany it as found in its native state, such as, for example, an intact biological system. An isolated nucleic acid molecule includes a nucleic acid molecule contained in cells that ordinarily express the nucleic acid molecule, but the nucleic acid molecule is present extrachromosomally or at a chromosomal location that is different from its natural chromosomal location.

The term "library" herein refers to a collection or plurality of template molecules, i.e., target DNA duplexes, which share common sequences at their 5' ends and common sequences at their 3' ends. Use of the term "library" to refer to a collection or plurality of template molecules should not be taken to imply that the templates making up the library are derived from a particular source, or that the "library" has a particular composition. By way of example, use of the term "library" should not be taken to imply that the individual templates within the library must be of different nucleotide sequence or that the templates must be related in terms of sequence and/or source.

A "methyl-dependent endonuclease" is a restriction endonuclease enzyme that requires specific methylated bases at the restriction site for cleavage of double-stranded DNA.

The term "mutation" herein refers to a change introduced into a parental sequence, including, but not limited to, substitutions, insertions, deletions (including truncations). The consequences of a mutation include, but are not limited to, the creation of a new character, property, function, phenotype or trait not found in the protein encoded by the parental sequence.

The term "nanopore" herein refers to a pore, channel or passage formed or otherwise provided in a membrane. A membrane may be an organic membrane, such as a lipid bilayer, or a synthetic membrane, such as a membrane formed of a polymeric material. The nanopore may be disposed adjacent or in proximity to a sensing circuit or an electrode coupled to a sensing circuit, such as, for example, a complementary metal oxide semiconductor (CMOS) or field effect transistor (FET) circuit. In some examples, a nanopore has a characteristic width or diameter on the order of 0.1 nm to about 1000 nm. Some nanopores are proteins. OmpG is an example of a protein nanopore.

The term "Next Generation Sequencing (NGS)" herein refers to sequencing methods that allow for massively parallel sequencing of clonally amplified and of single nucleic acid molecules during which a plurality, e.g., millions, of nucleic acid fragments from a single sample or from multiple different samples are sequenced in unison. Non-limiting examples of NGS include sequencing-by-synthesis, sequencing-by-ligation, real-time sequencing, and nanopore sequencing.

The term "nucleotide" herein refers to a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide. A sequence of polymeric operatively linked nucleotides is typically referred to herein as a "base sequence" or "nucleotide sequence," or nucleic acid or polynucleotide "strand," and is represented herein by a formula whose left to right orientation is in the conventional direction of 5'-terminus to 3'-terminus, referring to the terminal 5' phosphate group and the terminal 3' hydroxyl group at the "5'" and "3'" ends of the polymeric sequence, respectively.

The term "nucleotide analog" herein refers to analogs of nucleoside triphosphates, e.g., (S)-Glycerol nucleoside triphosphates (gNTPs) of the common nucleobases: adenine, cytosine, guanine, uracil, and thymidine (Horhota et al., Organic Letters, 8:5345-5347 [2006]). Also encompassed are nucleoside tetraphosphate, nucleoside pentaphosphates and nucleoside hexaphosphates. "Methylated nucleotides" are nucleotides that have been modified by addition of a methyl group (e.g., 3-methylcytosine, 3-methyladenine, N6-methyladenine). Methylated nucleotides are indicated herein with the letters "Me" in subscript after the one letter designation for the nucleotide base (e.g., $C_{Me}$). Nucleotide analogs include nucleotides that are resistant to exonuclease digestion, for example, thionated nucleotides. "Thionated" nucleotides include a phosphorothioate (PS) bond, substituting a sulfur atom for a non-bridging oxygen in the phosphate backbone of an oligonucleodie. This modification renders the internucleotide linkage resistant to nuclease degradation. Phosphorothioate bonds can be introduced between the last 3-5 nucleotides at the 5'- or 3'-end of an oligonucleotide to inhibit exonuclease degradation.

The term "operably linked" refers to a juxtaposition or arrangement of specified elements that allows them to perform in concert to bring about an effect. For example, a promoter is operably linked to a coding sequence if it controls the transcription of the coding sequence.

The term "polymerase" herein refers to an enzyme that catalyzes the polymerization of nucleotides (i.e., the polymerase activity). The term polymerase encompasses DNA polymerases, RNA polymerases, and reverse transcriptases. A "DNA polymerase" catalyzes the polymerization of deoxyribonucleotides. An "RNA polymerase" catalyzes the polymerization of ribonucleotides. A "reverse transcriptase" catalyzes the polymerization of deoxyribonucleotides that are complementary to an RNA template.

The terms "polynucleotide" and "nucleic acid" and "oligonucleotide" are herein used interchangeably to refer to a polymeric molecule composed of nucleotide monomers covalently bonded in a chain. DNA (deoxyribonucleic acid) and RNA (ribonucleic acid) are examples of polynucleotides. As used herein, the term polynucleotide refers to a polymeric form of nucleotides of any length and any three-dimensional structure and single- or multi-stranded (e.g., single-stranded, double-stranded, triple-helical, etc.), which contain deoxyribonucleotides, ribonucleotides, and/or analogs or modified forms of deoxyribonucleotides or ribonucleotides, including modified nucleotides or bases or their analogs. Because the genetic code is degenerate, more than one codon may be used to encode a particular amino acid, and the present invention encompasses polynucleotides which encode a particular amino acid sequence. Any type of modified nucleotide or nucleotide analog may be used, so long as the polynucleotide retains the desired functionality under conditions of use, including modifications that increase nuclease resistance (e.g., deoxy, 2'-O-Me, phosphorothioates, etc.). Labels may also be incorporated for purposes of detection or capture, for example, radioactive or nonradioactive labels or anchors, e.g., biotin. The term polynucleotide also includes peptide nucleic acids (PNA). Polynucleotides may be naturally occurring or non-naturally occurring. The terms "polynucleotide," "nucleic acid," and "oligonucleotide" are used herein interchangeably. Polynucleotides may contain RNA, DNA, or both, and/or modified forms and/or analogs thereof. A sequence of nucleotides may be interrupted by non-nucleotide components. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR.sub.2 ("amidate"), P(O)R, P(O)OR', CO or CH.sub.2 ("formacetal"), in which each R or R is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need and circular portions.

As used herein, "polypeptide" refers to a composition comprised of amino acids and recognized as a protein by those of skill in the art. The conventional one-letter or three-letter code for amino acid residues is used herein. The terms "polypeptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

The term "primer" herein refers to an oligonucleotide, whether occurring naturally or produced synthetically, which is capable of acting as a point of initiation of nucleic acid synthesis when placed under conditions in which synthesis of a primer extension product which is complementary to a nucleic acid strand is induced, e.g., in the presence of four different nucleotide triphosphates and a polymerase enzyme, e.g., a thermostable enzyme, in an appropriate buffer ("buffer" includes pH, ionic strength, cofactors, etc.) and at a suitable temperature. The primer is preferably single-stranded for maximum efficiency in amplification, but may alternatively be double-stranded. If double-stranded, the primer is first treated to separate its strands before being used to prepare extension products. Preferably, the primer is an oligodeoxyribonucleotide. The primer must be sufficiently long to prime the synthesis of extension products in the presence of the polymerase, e.g., thermostable polymerase enzyme. The exact lengths of a primer will depend on many factors, including temperature, source of primer and use of the method. For example, depending on the complexity of the target sequence, the oligonucleotide primer typically contains 15-25 nucleotides, although it may contain more or few nucleotides. Short primer molecules generally require colder temperatures to form sufficiently stable hybrid complexes with template.

A "promoter" refers to a regulatory sequence that is involved in binding RNA polymerase to initiate transcription of a gene. A promoter may be an inducible promoter or a constitutive promoter. An "inducible promoter" is a promoter that is active under environmental or developmental regulatory conditions.

The term "recombinant," refers to genetic material (i.e., nucleic acids, the polypeptides they encode, and vectors and cells comprising such polynucleotides) that has been modified to alter its sequence or expression characteristics, such as by mutating the coding sequence to produce an altered polypeptide, fusing the coding sequence to that of another gene, placing a gene under the control of a different promoter, expressing a gene in a heterologous organism, expressing a gene at a decreased or elevated levels, expressing a gene conditionally or constitutively in manner different from its natural expression profile, and the like. Generally recombinant nucleic acids, polypeptides, and cells based thereon, have been manipulated by man such that they are not identical to related nucleic acids, polypeptides, and cells found in nature.

The term "selective marker" or "selectable marker" refers to a gene capable of expression in a host cell that allows for ease of selection of those hosts containing an introduced nucleic acid or vector. Examples of selectable markers include but are not limited to antimicrobial substances (e.g., hygromycin, bleomycin, or chloramphenicol) and/or genes that confer a metabolic advantage, such as a nutritional advantage, on the host cell.

The term "sequencing library" herein refers to DNA that is processed for sequencing, e.g., using massively parallel methods, e.g., NGS. The DNA may optionally be amplified to obtain a population of multiple copies of processed DNA, which can be sequenced by NGS.

A "signal sequence" (also termed "presequence," "signal peptide," "leader sequence," or "leader peptide") refers to a sequence of amino acids bound to the N-terminal portion of a protein which facilitates the secretion of the mature form of the protein from the cell. The mature form of the extracellular protein lacks the signal sequence which is cleaved off during the secretion process.

The term "single stranded overhang" or "overhang" is used herein to refer to a strand of a double stranded (ds) nucleic acid molecule that extends beyond the terminus of the complementary strand of the ds nucleic acid molecule. The term "5' overhang" or "5' overhanging sequence" is used herein to refer to a strand of a ds nucleic acid molecule that extends in a 5' direction beyond the 3' terminus of the complementary strand of the ds nucleic acid molecule. The term "3' overhang" or "3' overhanging sequence" is used herein to refer to a strand of a ds nucleic acid molecule that extends in a 3' direction beyond the 5' terminus of the complementary strand of the ds nucleic acid molecule.

The phrases "substantially similar" and "substantially identical" in the context of at least two nucleic acids or polypeptides typically means that a polynucleotide or polypeptide comprises a sequence that has at least about 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or even 99.5% sequence identity, in comparison with a reference (e.g., wild-type) polynucleotide or polypeptide. Sequence identity may be determined using known programs such as BLAST, ALIGN, and CLUSTAL using standard parameters. (See, e.g., Altshul et al. (1990) J. Mol. Biol. 215:403-410; Henikoff et al. (1989) Proc. Natl. Acad. Sci. 89:10915; Karin et al. (1993) Proc. Natl. Acad. Sci. 90:5873; and Higgins et al. (1988) Gene 73:237). Software for performing BLAST analyses is publicly available through the National Center for Biotechnology Information. Also, databases may be searched using FASTA (Person et al. (1988) Proc. Natl. Acad. Sci. 85:2444-2448.) In some embodiments, substantially identical polypeptides differ only by one or more conservative amino acid substitutions. In some embodiments, substantially identical polypeptides are immunologically cross-reactive. In some embodiments, substantially identical nucleic acid molecules hybridize to each other under stringent conditions (e.g., within a range of medium to high stringency).

Nucleic acid "synthesis" herein refers to any in vitro method for making a new strand of polynucleotide or elongating an existing polynucleotide (i.e., DNA or RNA) in a template dependent manner Synthesis, according to the invention, can include amplification, which increases the number of copies of a polynucleotide template sequence with the use of a polymerase. Polynucleotide synthesis (e.g., amplification) results in the incorporation of nucleotides into a polynucleotide (e.g., extension from a primer), thereby forming a new polynucleotide molecule complementary to the polynucleotide template. The formed polynucleotide molecule and its template can be used as templates to synthesize additional polynucleotide molecules. "DNA synthesis," as used herein, includes, but is not limited to, polymerase chain reaction (PCR), and may include the use of labeled nucleotides, e.g., for probes and oligonucleotide primers, or for polynucleotide sequencing.

The term "tag" refers to a detectable moiety that may be one or more atom(s) or molecule(s), or a collection of atoms and molecules. A tag may provide an optical, electrochemical, magnetic, or electrostatic (e.g., inductive, capacitive) signature. A tag may block the flow of current through a nanopore.

The term "tagged nucleotide" herein refers to a nucleotide that includes a tag (or tag species) that is coupled to any location of the nucleotide including, but not limited to a phosphate (e.g., terminal phosphate), sugar or nitrogenous base moiety of the nucleotide. Tags may be one or more atom(s) or molecule(s), or a collection of atoms and molecules. A tag may provide an optical, electrochemical, magnetic, or electrostatic (e.g., inductive, capacitive) signature, which signature may be detected with the aid of a nanopore (US2014/013616). A tag can also be attached to a polyphosphate as is shown in FIG. 13 of US2014/013616.

The term "target DNA duplex" herein refers to a double stranded DNA molecule that is derived from a sample polynucleotide that is DNA, e.g., genomic or cell-free DNA, and/or RNA.

The term "template DNA molecule" herein refers to a strand of a nucleic acid from which a complementary nucleic acid strand is synthesized by a DNA polymerase, for example, in a primer extension reaction.

The term "template-dependent manner" refers to a process that involves the template dependent extension of a primer molecule (e.g., DNA synthesis by DNA polymerase). The term "template-dependent manner" typically refers to polynucleotide synthesis of RNA or DNA wherein the sequence of the newly synthesized strand of polynucleotide is dictated by the well-known rules of complementary base pairing (see, for example, Watson, J. D. et al., In: *Molecular Biology of the Gene*, 4th Ed., W. A. Benjamin, Inc., Menlo Park, Calif. (1987)).

As used herein, a "vector" refers to a polynucleotide sequence designed to introduce nucleic acids into one or more cell types. Vectors include cloning vectors, expression vectors, shuttle vectors, plasmids, phage particles, cassettes and the like.

Related (and derivative) proteins encompass "variant" proteins. Variant proteins differ from another (i.e., parental) protein and/or from one another by a small number of amino acid residues. A variant may include one or more amino acid mutations (e.g., amino acid deletion, insertion or substitution) as compared to the parental protein from which it is derived. In some embodiments, the number of different amino acid residues is any of about 1, 2, 3, 4, 5, 10, 20, 25, 30, 35, 40, 45, or 50. In some embodiments, variants differ by about 1 to about 10 amino acids. Alternatively or additionally, variants may have a specified degree of sequence identity with a reference protein or nucleic acid, e.g., as determined using a sequence alignment tool, such as BLAST, ALIGN, and CLUSTAL (see, infra). For example, variant proteins or nucleic acid may have at least about 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or even 99.5% amino acid sequence identity with a reference sequence.

As used herein, "wild-type," "native," and "naturally-occurring" proteins are those found in nature. The terms "wild-type sequence" refers to an amino acid or nucleic acid sequence that is found in nature or naturally occurring. In some embodiments, a wild-type sequence is the starting point of a protein engineering project, for example, production of variant proteins.

Adaptors

Adaptors for polynucleotide sequencing are provided herein. The adaptors contain a double-stranded polynucleotide duplex (e.g., DNA duplex) region that has a portion of a recognition sequence for a methyl-dependent restriction endonuclease at its end. Two adaptors that covalently link together (e.g., ligate) at the ends of their respective polynucleotide duplex regions, i.e., forming an adaptor dimer, will form a complete sequence for the methyl-dependent endonuclease, and will be subject to cleavage in the presence of the endonuclease. Adaptors that covalently link to the ends of target polynucleotide duplexes to be sequenced will not be subject to cleavage by the endonuclease except in the rare instance where the end of the target polynucleotide contains the remaining sequences for the endonuclease recognition site.

Figure 1:
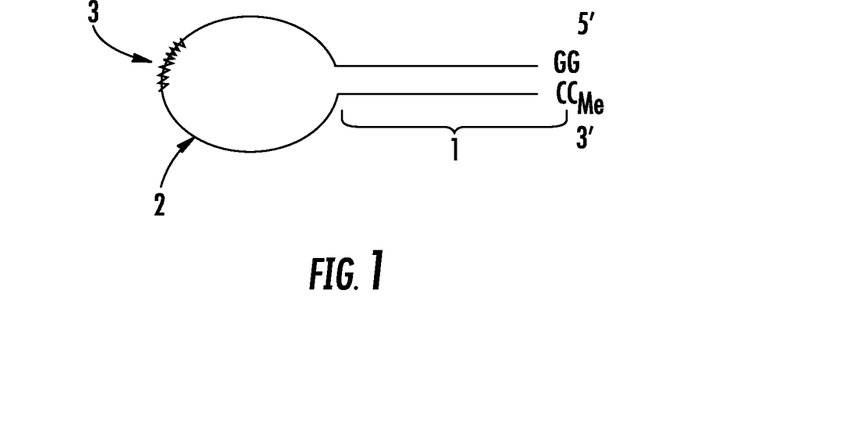
FIG. 1 shows an embodiment of an adaptor with a double-stranded polynucleotide duplex region and a single-stranded hairpin region.

In some embodiments, as shown schematically in FIG. 1, an adaptor includes a single-stranded hairpin region 2 and the double-stranded polynucleotide duplex region 1 with a portion of the methyl-dependent endonuclease sequence at the end of the duplex region. Optionally, the single-stranded hairpin region includes a primer binding sequence 3.

Figure 2:
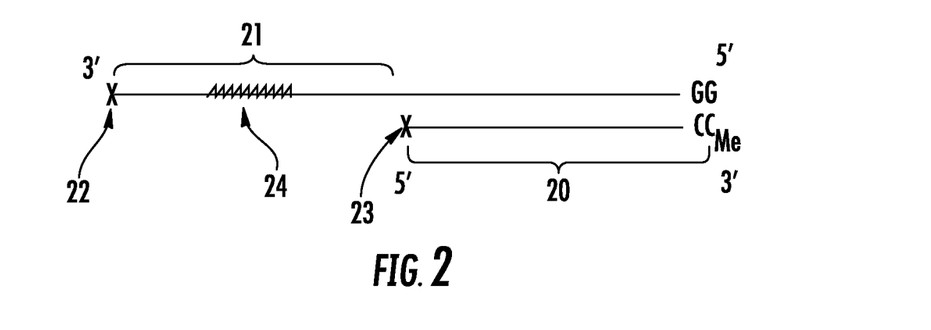
FIG. 2 shows an embodiment of a linear adaptor with a double-stranded polynucleotide duplex region and a 3' overhang region.

In some embodiments, as shown schematically in FIG. 2, an adaptor is a linear polynucleotide (e.g., DNA) that contains first and second polynucleotide (e.g., DNA) strands and first and second ends. The first end includes the double-stranded polynucleotide duplex 20 with a portion of the methyl-dependent endonuclease sequence. The second end includes a single-stranded 3' overhang region 21 with one or more modified nucleotide 22 that is resistant to exonuclease digestion (e.g., thionated nucleotide(s)) at or near the 3' end of the first strand and one or more modified nucleotide 23 that is resistant to exonuclease digestion (e.g., thionated nucleotide(s)) at or near the 5' end of the second strand, which is part of the double-stranded polynucleotide duplex region. Optionally, the single-stranded 3' overhang includes one or more primer binding sequence(s) 24. In some embodiments, the single-stranded 3' overhang region 21 is 8 to about 100 nucleotides in length.

In some embodiments, the double-stranded polynucleotide duplex region of the adaptor includes the sequence GG at the 5' end and $CC_{Me}$ at the 3' end, forming the sequence $CC_{Me}GG$ when two adaptors are linked together. This sequence is a recognition sequence for methyl-dependent endonucleases MspI or MspII.

In some embodiments, the double-stranded polynucleotide duplex region of the adaptor includes the sequence TC at the 5' end and $GA_{Me}$ at the 3' end, forming the sequence $GA_{Me}TC$ when two adaptors are linked together. This sequence is a recognition sequence for methyl-dependent endonucleases DpnI or DpnII.

Target Polynucleotides

A nucleic acid sample to which the methods described herein may be applied may be derived from a biological sample such as a tissue sample, a biological fluid sample, or a cell sample, and processed fractions thereof. A biological fluid sample includes, as non-limiting examples, blood, plasma, serum, sweat, tears, sputum, urine, ear flow, lymph, interstitial fluid, saliva, cerebrospinal fluid, ravages, bone marrow suspension, vaginal flow, transcervical lavage, brain fluid, ascites, milk, secretions of the respiratory, intestinal and genitourinary tracts, amniotic fluid and leukophoresis samples. In some embodiments, the source sample is a sample that is easily obtainable by non-invasive procedures, e.g., blood, plasma, serum, sweat, tears, sputum, urine, ear flow, and saliva. IN some embodiments, the biological sample is a peripheral blood sample, or the plasma and serum fractions. In other embodiments, the biological sample is a swab or smear, a biopsy specimen, or a cell culture. In another embodiment, the sample is a mixture of two or more biological samples, e.g., a biological sample comprising two or more of a biological fluid sample, a tissue sample, and a cell culture sample. As used herein, the terms "blood," "plasma," and "serum" encompass fractions or processed portions thereof. Similarly, where a sample is taken from a biopsy, swab, smear, etc., the "sample" may encompass a processed fraction or portion derived from the biopsy, swab, smear, etc.

In some embodiments, samples can be obtained from sources, including, but not limited to, samples from different individuals, different developmental stages of the same or different individuals, different diseased individuals (e.g., individuals with cancer or suspected of having a genetic disorder), normal individuals (e.g., individuals lacking a condition of interest), samples obtained at different stages of a disease in an individual, samples obtained from an individual subjected to different treatments for a disease, samples from individuals subjected to different environmental factors, individuals with predisposition to a pathology, individuals with exposure to a pathogen such as an infectious disease agent (e.g., HIV), and individuals who are recipients of donor cells, tissues and/or organs. In some embodiments, the sample is a sample comprising a mixture of different source samples derived from the same or different subjects. For example, a sample can include a mixture of cells derived from two or more individuals, as is often found at crime scenes. In one embodiment, the sample is a maternal sample that is obtained from a pregnant female, for example a pregnant woman. In this instance, the sample can be analyzed using the methods described herein to provide a prenatal diagnosis of potential fetal disorders. Unless otherwise specified, a maternal sample includes a mixture of fetal and maternal DNA, e.g., cfDNA. In some embodiments, the maternal sample is a biological fluid sample, e.g., blood sample. In other embodiments, the maternal sample is a purified cfDNA sample.

A sample can be an unprocessed biological sample, e.g., a whole blood sample. A source sample can be a partially processed biological sample, e.g., a blood sample that has been fractionated to provide a substantially cell-free plasma fraction. A source sample can be a biological sample containing purified nucleic acids, e.g., a sample of purified cfDNA derived from an essentially cell-free plasma sample. Processing of the samples can include, for example, freezing, (e.g., tissue biopsy samples), fixing (e.g., formalin-fixing), and embedding, (e.g., paraffin-embedding). Partial processing of samples can include, for example, sample fractionation (e.g., obtaining plasma fractions from blood samples), and other processing steps required for analyses of samples collected during routine clinical work, such as in the context of clinical trials, and/or scientific research. Additional processing steps can include, for example, steps for isolating and purifying sample nucleic acids. Further processing of purified samples can include, for example, steps for the requisite modification of sample nucleic acids in preparation for sequencing. In some embodiments, the sample is an unprocessed or a partially processed sample.

Samples can also be obtained from in vitro cultured tissues, cells, or other polynucleotide-containing sources. The cultured samples can be taken from sources including, but not limited to, cultures (e.g., tissue or cells) maintained in various media and conditions (e.g., pH, pressure, temperature), maintained for different periods of time, or treated with different factors or reagents (e.g., a drug candidate, or a modulator).

Biological samples can be obtained from a variety of subjects, including but not limited to, human beings, and other organisms, including mammals, plants, or cells from the subjects, microorganisms (e.g., bacteria, fungi), or viruses.

Sample polynucleotides that can be analyzed as described herein include genomic cellular DNA, cell-free DNA (cfDNA), mitochondrial DNA, RNA, and cDNA. Preparation of sequencing libraries for some NGS sequencing platforms require that the polynucleotides be of a specific range of fragment sizes, and require that large polynucleotides, e.g., cellular genomic DNA, be fragmented. Therefore, fragmentation of polynucleotides, e.g., cellular genomic DNA may be required. Fragmentation of polynucleotide molecules by mechanical means cleaves the DNA backbone at C—O, P—O and C—C, resulting in a heterogeneous mix of blunt and 3'- and 5'-overhanging ends with broken C—O, P—O and/C—C bonds, which need to be repaired for the subsequent enzymatic reactions, e.g., ligation of sequencing adaptors, that are required for preparing DNA for sequencing. Alternatively, fragmentation of cfDNA, which exists as fragments of <300 base may not be necessary for generating a sequencing library using cfDNA samples. Once the starting DNA or cDNA has been fragmented, the fragments are blunted i.e. end-repaired.

In some embodiments, a nucleic acid to be sequenced is extended with standard, unmethylated nucleotide bases to produce a cDNA extension product. If the nucleic acid target contains methylated nucleotides, the duplex that is produced with the cDNA will not contain an internal recognition sequence for a methyl-dependent endonuclease, since methylated nucleotides are required on both strands, and the double-stranded nucleic acid thus produced will not be cleaved internally by the endonuclease. If there is a methylated base at or near the end of the target nucleic acid, and ligation of the end of the target duplex with an adaptor, as described herein, results in production of a recognition sequence for the methyl-dependent endonuclease, the adaptor may be cleaved from the target during cleavage of adaptor dimers, but this is expected to be a rare event.

In some embodiments, a nucleic acid to be sequenced is amplified, e.g., amplified by an amplification procedure such as, for example, polymerase chain reaction (PCR). Amplification of a nucleic acid sample that contains methylated bases (e.g., genomic DNA) with standard, unmethylated nucleotide bases, will result in DNA products that do not contain methylated bases. Such amplified target DNA will not contain a restriction site for a methyl-dependent endonuclease, and will not be cleaved when the sample is treated with such an endonuclease for removal of adaptor dimers, as described herein.

Preparing Target Polynucleotides for Sequencing

Figure 3:
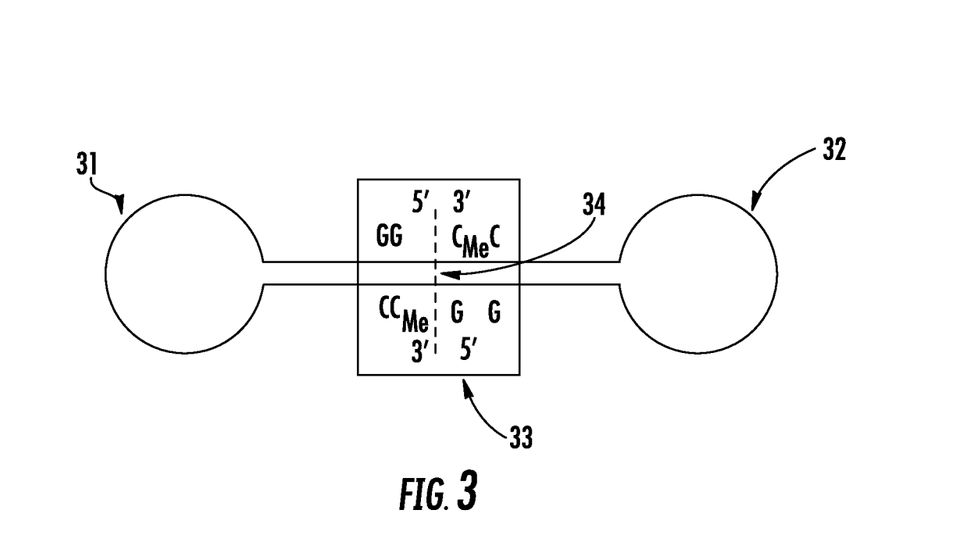
FIG. 3 shows an embodiment in which two adaptors are ligated together to form an adaptor dimer that includes a complete recognition sequence for a methyl-dependent endonuclease.

Methods are provided herein for preparing target polynucleotide duplexes for sequencing. Each end of a target polynucleotide duplex is covalently linked to the double-stranded polynucleotide duplex region of a sequencing adaptor, as described herein. Adaptor-linked target polynucleotide duplexes are produced, with a sequencing adaptor at each end. Adaptor dimers may also be produced, as shown schematically in FIG. 3. The adaptor dimers include two adaptors 31 and 32 that are ligated together at the ends of the double-stranded polynucleotide duplex regions of each adaptor, shown schematically as dashed line 34 in FIG. 3. The ligation of the two adaptors produces restriction site 33 for a methyl-dependent endonuclease. The sample mixture is then treated with a methyl-dependent endonuclease, and adaptor dimers that include the restriction sequence for the endonuclease, as described above, are cleaved. The sample mixture is then treated with one or more exonuclease(s) which depolymerize the cleaved adaptors from their free 5' and/or 3' ends, thus removing the adaptor dimers and any free unligated adaptors from the mixture of polynucleotides to be sequenced. Adaptors that are ligated to the ends of target polynucleotide duplexes do not have a free end that is susceptible to exonuclease digestion. As described above, the adaptors either have a hairpin loop or in the case of a linear adaptor, modified nucleotides, e.g., thionated nucleotides, at their unligated ends, such that they will not be digested by an exonuclease.

In some embodiments, target polynucleotides are prepared for sequencing in accordance with the methods disclosed herein, and after methyl-dependent endonuclease and exonuclease treatment, the sample mixture that contains adaptor-linked target polynucleotide duplexes contains less than about 1%, 0.5%, 0.2%, 0.1%, 0.05%, or 0.01% adaptor dimers. In some embodiments, the sample mixture contains no or substantially no adaptor dimers.

Methyl-Dependent Endonucleases

A number of methyl-dependent endonuclease enzymes are known. In one embodiment, the methyl-dependent endonuclease is MspI or MspII, which cleaves double-stranded DNA at the palindromic restriction sequence $CC_{Me}GG$. In another embodiment, the methyl-dependent endonuclease is DpnI or DpnII, which cleaves double-stranded DNA at the palindromic restriction sequence $GA_{Me}TC$. It will be appreciated that any methyl-dependent endonuclease may be of use in the methods described herein if it cleaves at a recognition sequence that includes at least one methylated nucleotide and that may be produced by the ligation of nucleotide sequences at the ends of duplex regions of adaptors as described herein to provide the complete recognition sequence for the enzyme.

Methods for Sequencing

Methods are provided for sequencing polynucleotides. Polynucleotide duplexes are prepared for sequencing by covalently linking adaptors as described herein at each end. Adaptor dimers are removed as described herein, resulting in a sequencing mixture that contains less than about 1%, 0.5%, 0.2%, 0.1%, 0.05%, or 0.01% adaptor dimers. In some embodiments, the sample mixture contains no or substantially no adaptor dimers.

In some embodiments, the method includes sequencing a polynucleotide sample that includes a plurality of adaptor-linked DNA duplexes with a sequencing adaptor as described herein linked at each end of the target duplex, wherein the polynucleotide sample contains less than about 1%, 0.5%, 0.2%, 0.1%, 0.05%, or 0.01% adaptor dimers, or no or substantially no adaptor dimers.

In some embodiments, a primer is hybridized to a primer binding sequence on the adaptor and extended with a DNA polymerase enzyme, thereby preparing a primer extension product for sequencing. In some embodiments, the primer is extended to produce a complementary copy of one strand of the target polynucleotide duplex, and the copy is sequenced as it is synthesized by the polymerase.

A number of polynucleotide sequencing methods are known in the art. Sequencing methods that can be used include Next Generation Sequencing (NGS) technologies, which allow multiple samples to be sequenced individually (i.e., singleplex sequencing) or as pooled samples as indexed target DNA molecules (i.e., multiplex sequencing) in a single sequencing run, and generate up to several hundred million reads of DNA sequences. Sequences of target nucleic acids, and of indexed target nucleic acids can be determined using NGS methods in which clonally amplified DNA templates or single DNA molecules, respectively, are sequenced in a massively parallel fashion (e.g., as described in Voelkerding et al. (2008) *Clin Chem* 55:641-658; Metzker (2010) *Nature Rev* 11:31-46. NGS technologies are sometimes subclassified as First, Second and Third Generation Sequencing (Pareek and Smoczynski (2011) *J Appl Genetics* 52:413-435). In addition to high-throughput sequence information, NGS provides quantitative information, in that each sequence read can be a countable "sequence tag" representing an individual clonal DNA template or a single DNA molecule. The sequencing technologies of NGS include, without limitation, pyrosequencing, sequencing-by-synthesis with reversible dye terminators, sequencing by oligonucleotide probe ligation, ion semiconductor sequencing, and nanopore sequencing.

The major steps involved in NGS that are generally applicable to all of the current technologies are library choice/construction, preparation of libraries for sequencing, and massively parallel sequencing.

In one embodiment, the present method can be applied to 454 sequencing (http://www.454.com/) (e.g. as described in Margulies, M. et al. (2005) *Nature* 437:376-380). The overall approach for 454 is pyrosequencing based. The sequencing preparation begins with lengths of DNA (e.g., amplicons or nebulized genomic/metagenomic DNA) that have adaptors on either end. These are fixed to tiny beads (ideally, one bead will have one DNA fragment) that are suspended in a water-in-oil emulsion. An emulsion PCR step is then performed to make multiple copies of each DNA fragment, resulting in a set of beads in which each one contains many cloned copies of the same DNA fragment. A fiber-optic chip filled with a field of microwells, known as a PicoTiterPlate, is then washed with the emulsion, allowing a single bead to drop into each well. The wells are also filled with a set of enzymes for the sequencing process (e.g., DNA polymerase, ATP sulfurylase, and luciferase). At this point, sequencing-by-synthesis can begin, with the addition of bases triggering pyrophosphate release, which produces flashes of light that are recorded to infer the sequence of the DNA fragments in each well as each base type (A, C, G, T) is added.

In another embodiment, the present method can be applied to Illumina sequencers. Illumina sequencing is a sequencing-by-synthesis method, which differs from that of the 454 in two major ways: (1) it uses a flow cell with a field of oligonucleotides attached, instead of a chip containing individual microwells with beads, and (2) it does not involve pyrosequencing, but rather reversible dye terminators. The dye-termination approach resembles the "traditional" Sanger sequencing. It is different from Sanger, however, in that the dye terminators are reversible, so they are removed after each imaging cycle to make way for the next reversible dye-terminated nucleotide. Sequencing preparation begins with lengths of DNA that have specific adaptors on either end being washed over a flow cell filled with specific oligonucleotides that hybridize to the ends of the fragments. Each fragment is then replicated to make a cluster of identical fragments. Reversible dye-terminator nucleotides are then washed over the flow cell and given time to attach; the excess nucleotides are washed away, the flow cell is imaged, and the terminators are reversed so that the process can repeat and nucleotides can continue to be added in subsequent cycles.

In another embodiment, the present method can be applied the Applied Biosystems SOLiD process (http://solid.appliedbiosystems.com). The SOLiD process begins with an emulsion PCR step akin to the one used by 454, but the sequencing itself is entirely different from the previously described systems. Sequencing involves a multiround, staggered, dibase incorporation system. DNA ligase is used for incorporation, making it a "sequencing-by-ligation" approach, as opposed to the "sequencing-by-synthesis" approaches mentioned previously. Mardis, E. R. (2008) *Annu Rev Genomics Hum Genet* 9:387-402, provides a thorough overview of the complex sequencing and decoding processes involved with using this system.

In another embodiment, the present method can be applied the Ion Torrent system (http://www.iontorrent-.com/). The Ion Torrent system begins in a manner similar to 454, with a plate of microwells containing beads to which DNA fragments are attached. It differs from all of the other systems, however, in the manner in which base incorporation is detected. When a base is added to a growing DNA strand, a proton is released, which slightly alters the surrounding pH. Microdetectors sensitive to pH are associated with the wells on the plate, which is itself a semiconductor chip, and they record when these changes occur. As the different bases (A, C, G, T) are washed sequentially through, additions are recorded, allowing the sequence from each well to be inferred.

In another embodiment, the present method can be applied the PacBio single-molecule, real-time sequencing approach (http://www.pacificbiosciences.com/). The PacBio sequencing system involves no amplification step, setting it apart from other major NGS systems. The sequencing is performed on a chip containing many zero-mode waveguide (ZMW) detectors. DNA polymerases are attached to the ZMW detectors and phospholinked dye-labeled nucleotide incorporation is imaged in real time as DNA strands are synthesized. PacBio's RS II C2 XL currently offers both the greatest read lengths (averaging around 4,600 bases) and the highest number of reads per run (about 47,000). The typical "paired-end" approach is not used with PacBio, since reads are typically long enough that fragments, through CCS, can be covered multiple times without having to sequence from each end independently. Multiplexing with PacBio does not involve an independent read, but rather follows the standard "in-line" barcoding model.

In another embodiment, the present method can be applied to nanopore sequencing (e.g., as described in Soni, G. V. and Meller, A. (2007) *Clin Chem* 53:1996-2001). Nanopore sequencing DNA analysis techniques have been developed by a number of companies, including Oxford Nanopore Technologies (Oxford, United Kingdom), Roche, and Illumina. In one embodiment, sequencing by synthesis is used, whereby the nucleotides that are incorporated into the growing copy of a DNA molecule are labeled with a polymer tag that is unique to each nucleotide type: A, G, C, and T. During incorporation of the labeled nucleotides during enzymatic extension of the new strand, the polymer tags are caught in the pore and the blockage of ionic current by the tag designates the base that is being incorporated. Successive nucleotide incorporations during strand synthesis lead to successive polymer ag captures allowing the new strand sequence to be detected.

Kits

Kits are provided for use in the methods described herein. The kits include sequencing adaptors as described herein. Optionally, instructions for use, e.g., for preparing target polynucleotide duplexes for sequencing, are provided. Instructions may be provided in printed form or in the form of an electronic medium such as a CD, DVD, or USB, or in the form of a website address where such instructions may be obtained. Optionally, other components for preparing target polynucleotide duplexes for sequencing and/or sequencing reagents, may be included. For example, a kit may include one or more of: a ligase enzyme; a methyl-dependent endonuclease enzyme; one or more exonuclease enzyme(s); and one or more sequencing primer(s).

Suitable packaging is provided. As used herein, "packaging" refers to a solid matrix or material customarily used in a system and capable of holding within fixed limits a composition. Such materials include glass and plastic (e.g., polyethylene, polypropylene, and polycarbonate) bottles, vials, paper, plastic, and plastic-foil laminated envelopes and the like.

Although the foregoing invention has been described in some detail by way of illustration and examples for purposes of clarity of understanding, it will be apparent to those skilled in the art that certain changes and modifications may be practiced without departing from the spirit and scope of the invention. Therefore, the description should not be construed as limiting the scope of the invention.

All publications, patents, and patent applications cited herein are hereby incorporated by reference in their entireties for all purposes and to the same extent as if each individual publication, patent, or patent application were specifically and individually indicated to be so incorporated by reference.

We claim:

1. A method for preparing target DNA duplexes for sequencing, wherein the method comprises:
   (a) a step of either: (i) extending the target DNA duplexes with standard unmethylated nucleotide bases, or (ii) amplifying the target DNA duplexes with standard unmethylated nucleotide bases;
   (b) providing a plurality of sequencing adaptors, wherein each of the plurality of sequencing adaptors comprises a single-stranded polynucleotide hairpin region and a double-stranded polynucleotide duplex region, wherein the double-stranded polynucleotide duplex region contains a portion of a recognition sequence for a methyl-dependent endonuclease at one of its ends, and wherein a complete recognition sequence will be formed if the duplex regions of two adaptors are covalently linked together to produce an adaptor dimer;
   (c) covalently linking the duplex regions of the sequencing adaptors to first and second ends of a plurality of blunt-ended target DNA duplexes, thereby producing adaptor-linked target DNA duplexes; and
   (d) removing adaptor dimers, if any, by digestion with a methyl-dependent endonuclease, followed by digestion with one or more exonuclease(s).

2. The method of claim 1, wherein the double-stranded polynucleotide duplex region in each of the plurality of sequencing adaptors comprises a first strand comprising a 5' end hybridized to a second strand comprising a 3' end, wherein the first strand comprises the sequence GG at the 5' end hybridized to the sequence $CC_{Me}$ at the 3' end of the second strand.

3. The method of claim 2, wherein the methyl-dependent endonuclease is MspI or MspII, and wherein the adaptor dimers comprise the recognition sequence $CC_{Me}GG$.

4. The method of claim 1, wherein the double-stranded polynucleotide duplex region in each of the plurality of sequencing adaptors comprises a first strand comprising a 5' end hybridized to a second strand comprising a 3' end, wherein the first strand comprises the sequence TC at the 5' end hybridized to the sequence $GA_{Me}$ at the 3' end.

5. The method of claim 4, wherein the methyl-dependent endonuclease is DpnI or DpnII, and wherein the adaptor dimers comprise the recognition sequence $GA_{Me}$ TC.

6. The method of claim 1, wherein the one or more exonuclease(s) is selected from Exonuclease VII, Exonuclease III, and TS Exonuclease.

7. A method for preparing a sample comprising target DNA duplexes for sequencing, wherein the method comprises the method for preparing target DNA duplexes for sequencing of claim 1, and wherein the sample comprises less than 1% adaptor dimers.

8. A method for sequencing polynucleotides, wherein the method comprises the method for preparing target DNA duplexes for sequencing according to claim 1,
   wherein the single-stranded hairpin region of each of the plurality of sequencing adaptors comprises a primer-binding sequence, and
   wherein the method further comprises:
   (e) sequencing polynucleotides by hybridizing a primer to the primer-binding sequence and extending the primer with a DNA polymerase enzyme, thereby synthesizing a complementary copy of one strand of the adaptor-linked target DNA, and wherein the copy of the one strand is sequenced as it is synthesized.

9. A method for sequencing DNA duplexes, wherein the method comprises:
   (a) a step of either: (i) extending the target DNA duplexes with standard unmethylated nucleotide bases, or (ii) amplifying the target DNA duplexes with standard unmethylated nucleotide bases;
   (b) providing a plurality of sequencing adaptors, wherein each of the plurality of sequencing adaptors comprises a double-stranded polynucleotide duplex region, wherein the double-stranded polynucleotide duplex region contains a portion of a recognition sequence for a methyl-dependent endonuclease at its end, and wherein a complete recognition sequence will be formed if the duplex regions of two adaptors are covalently linked together to produce an adaptor dimer;
(c) covalently linking the double-stranded polynucleotide duplex regions of the plurality of sequencing adaptors to target DNA duplexes, thereby producing adaptor-linked DNA duplexes;
(d) removing adaptor dimers, if any, by digestion with a methyl-dependent endonuclease followed by digestion with one or more exonuclease(s); and
(e) sequencing the adaptor linked DNA duplexes, and wherein either:
  (1) each of the plurality of sequencing adaptors further comprises a single-stranded polynucleotide hairpin region, or
  (2) each of the plurality of sequencing adaptors is a linear polynucleotide comprising a first and second nucleotide strand, wherein each of the plurality of sequencing adaptors comprises: (i) a first end comprising the double-stranded polynucleotide duplex region, and (ii) a second end comprising a 3' end of the first polynucleotide strand and a 5' end of the second polynucleotide strand, wherein the first polynucleotide strand comprises a single-stranded 3' overhang region comprising a thionated nucleotide at its 3' end, and wherein the second polynucleotide strand comprises a thionated nucleotide at its 5' end.

10. The method of claim 9, wherein the plurality of sequencing adaptors further comprises a sequencing primer-binding sequence.

11. A method for preparing target DNA duplexes for sequencing, wherein the method comprises:
(a) a step of either: (i) extending the target DNA duplexes with standard unmethylated nucleotide bases, or (ii) amplifying the target DNA duplexes with standard unmethylated nucleotide bases;
(b) providing a plurality of sequencing adaptors, wherein each of the plurality of sequencing adaptors comprises a double-stranded polynucleotide duplex region, wherein the double-stranded polynucleotide duplex region contains a portion of a recognition sequence for a methyl-dependent endonuclease at one of its ends, and wherein a complete recognition sequence will be formed if the duplex regions of two adaptors are covalently linked together to produce an adaptor dimer;
(c) covalently linking the duplex regions of the sequencing adaptors to first and second ends of a plurality of blunt-ended target DNA duplexes, thereby producing adaptor-linked target DNA duplexes; and
(d) removing adaptor dimers, if any, by digestion with a methyl-dependent endonuclease, followed by digestion with one or more exonuclease(s), and wherein
each of the plurality of sequencing adaptors is a linear polynucleotide comprising a first and second polynucleotide strand, wherein each of the plurality of sequencing adaptors comprises: (i) a first end comprising the double-stranded polynucleotide duplex region, and (ii) a second end comprising a 3' end of the first polynucleotide strand and a 5' end of the second polynucleotide strand, wherein the first polynucleotide strand comprises a single-stranded 3' overhang region comprising a thionated nucleotide at its 3' end, and wherein the second polynucleotide comprises a thionated nucleotide at its 5' end.

12. The method of claim 11, wherein the double-stranded polynucleotide duplex region in each of the plurality of sequencing adaptors comprises a first strand comprising a 5' end hybridized to a second strand comprising a 3' end, wherein the first strand comprises the sequence GG at the 5' end hybridized to the sequence $CC_{Me}$ at the 3' end of the second strand.

13. The method of claim 12, wherein the methyl-dependent endonuclease is MspI or MspII, and wherein the adaptor dimers comprise the recognition sequence $CC_{Me}GG$.

14. The method of claim 11, wherein the double-stranded polynucleotide duplex region in each of the plurality of sequencing adaptors comprises a first strand comprising a 5' end hybridized to a second strand comprising a 3' end, wherein the first strand comprises the sequence TC at the 5' end hybridized to the sequence $GA_{Me}$ at the 3' end.

15. The method of claim 14, wherein the methyl-dependent endonuclease is DpnI or DpnII, and wherein the adaptor dimers comprise the recognition sequence $GA_{Me}$ TC.

16. The method of claim 11, wherein the one or more exonuclease(s) is selected from Exonuclease VII, Exonuclease III, and T5 Exonuclease.

17. A method for preparing a sample comprising target DNA duplexes for sequencing, wherein the method comprises the method for preparing target DNA duplexes for sequencing of claim 11, and wherein the sample comprises less than 1% adaptor dimers.

18. A method for sequencing polynucleotides, wherein the method comprises the method for preparing target DNA duplexes for sequencing according to claim 11,
wherein the single-stranded 3' overhang region comprises a primer-binding sequence, and
wherein the method further comprises:
(e) sequencing polynucleotides by hybridizing a primer to the primer-binding sequence and extending the primer with a DNA polymerase enzyme, thereby synthesizing a complementary copy of one strand of the adaptor-linked target DNA, and wherein the copy of the one strand is sequenced as it is synthesized.

* * * * *